United States Patent
Sørensen

(10) Patent No.: US 11,382,490 B2
(45) Date of Patent: Jul. 12, 2022

(54) TIP PART FOR A VISION DEVICE

(71) Applicant: AMBU A/S, Ballerup (DK)

(72) Inventor: Morten Sørensen, Ballerup (DK)

(73) Assignee: AMBU A/S, Ballerup (DK)

( * ) Notice: Subject to any disclaimer, the term of this patent is extended or adjusted under 35 U.S.C. 154(b) by 40 days.

(21) Appl. No.: 16/550,053

(22) Filed: Aug. 23, 2019

(65) Prior Publication Data
US 2020/0060521 A1 Feb. 27, 2020

(30) Foreign Application Priority Data

Aug. 24, 2018 (EP) .................................... 18190733

(51) Int. Cl.
A61B 1/00 (2006.01)
A61B 1/07 (2006.01)
A61B 1/05 (2006.01)

(52) U.S. Cl.
CPC .......... *A61B 1/00096* (2013.01); *A61B 1/051* (2013.01); *A61B 1/07* (2013.01)

(58) Field of Classification Search
CPC ..................... G02B 23/2407; G02B 23/2423
See application file for complete search history.

(56) References Cited

U.S. PATENT DOCUMENTS

| 4,805,596 | A | 2/1989 | Hatori |
| 5,193,525 | A | 3/1993 | Silverstein et al. |
| 5,718,663 | A | 2/1998 | Wulfsberg |
| 5,879,289 | A | 3/1999 | Yarush et al. |
| 5,993,378 | A | 11/1999 | Lemelson |
| 6,503,196 | B1 * | 1/2003 | Kehr ................. A61B 1/00096 600/129 |
| 7,442,167 | B2 * | 10/2008 | Dunki-Jacobs ...... A61B 1/0653 600/129 |

(Continued)

FOREIGN PATENT DOCUMENTS

| EP | 0 75 6 845 | 2/1997 |
| JP | H 03264037 | 11/1991 |

(Continued)

OTHER PUBLICATIONS

Extended Search Report in related European Application No. 18190733.8 dated Feb. 1, 2019.
European Search Report in EP 18190736, dated Feb. 11, 2019.

Primary Examiner — Michael J Carey
Assistant Examiner — Minqiao Huang
(74) Attorney, Agent, or Firm — Faegre Drinker Biddle & Reath LLP

(57) ABSTRACT

A tip part for an endoscope has a vision receptor; a first light source; an exterior housing accommodating the vision receptor and the first light source; the exterior housing comprising a window positioned at a distal end of the tip part, the window being of a transparent material, the window comprising an exterior front surface positioned at least partly in front of the vision receptor and the first light source, wherein the window integrally comprises a first optical well of the transparent material, the first optical well being an interior protrusion positioned between the first light source and the vision receptor so that a portion of light emitted from the first light source and reflected from the exterior surface enters the first optical well, whereby stray light is at least partially prevented from entering the vision receptor.

22 Claims, 5 Drawing Sheets

(56) References Cited

U.S. PATENT DOCUMENTS

| | | | |
|---|---|---|---|
| 7,662,094 B2 * | 2/2010 | Iddan | A61B 1/00096 600/176 |
| 8,414,480 B2 | 4/2013 | Kendale et al. | |
| 8,485,966 B2 | 7/2013 | Robertson | |
| 8,790,250 B2 | 7/2014 | Petersen et al. | |
| 9,220,400 B2 | 12/2015 | Petersen | |
| 9,521,942 B2 | 12/2016 | Robertson | |
| 9,622,649 B2 | 4/2017 | Lin | |
| 9,854,962 B2 | 1/2018 | McGrail et al. | |
| 10,245,402 B2 | 4/2019 | Daher et al. | |
| 10,321,804 B2 | 6/2019 | Jacobsen et al. | |
| 2003/0227547 A1 * | 12/2003 | Iddan | A61B 1/051 348/151 |
| 2004/0064018 A1 | 4/2004 | Dunki-Jacobs et al. | |
| 2004/0199052 A1 | 10/2004 | Banik et al. | |
| 2004/0242963 A1 | 12/2004 | Matsumoto et al. | |
| 2005/0203341 A1 | 9/2005 | Welker et al. | |
| 2006/0281972 A1 * | 12/2006 | Pease | A61B 1/0684 600/109 |
| 2008/0242935 A1 | 10/2008 | Inoue | |
| 2009/0054728 A1 | 2/2009 | Trusty | |
| 2009/0177040 A1 | 7/2009 | Lyons et al. | |
| 2009/0209819 A1 | 8/2009 | Kitagawa et al. | |
| 2010/0286475 A1 | 11/2010 | Robertson | |
| 2011/0118549 A1 | 5/2011 | Han | |
| 2011/0245617 A1 | 10/2011 | Kitano | |
| 2012/0065469 A1 * | 3/2012 | Allyn | A61B 1/005 600/109 |
| 2012/0323078 A1 | 12/2012 | Kikumori et al. | |
| 2013/0131447 A1 * | 5/2013 | Benning | A61B 1/00101 600/109 |
| 2013/0175720 A1 | 7/2013 | Otsuka et al. | |
| 2013/0271588 A1 | 10/2013 | Kirma et al. | |
| 2014/0081085 A1 | 3/2014 | Takato et al. | |
| 2015/0335227 A1 | 11/2015 | Jacobsen et al. | |
| 2015/0351620 A1 * | 12/2015 | Ruppersberg | A61B 1/00193 600/200 |
| 2016/0106306 A1 | 4/2016 | Furuta | |
| 2017/0245734 A1 | 8/2017 | Kaneko | |
| 2018/0132700 A1 | 5/2018 | Ouyang et al. | |
| 2018/0143421 A1 | 5/2018 | Hegenbarth et al. | |
| 2018/0310890 A1 | 11/2018 | Li | |
| 2019/0175007 A1 | 6/2019 | Sørensen et al. | |

FOREIGN PATENT DOCUMENTS

| | | |
|---|---|---|
| JP | 2004016455 | 1/2004 |
| JP | 3764512 | 4/2006 |
| JP | 2009-125528 | 6/2009 |
| JP | 2010169802 | 8/2010 |
| JP | 2013009896 | 1/2013 |
| JP | 2018015250 | 2/2018 |
| WO | WO 2005/023099 | 3/2005 |
| WO | WO 2008/115575 | 9/2008 |
| WO | WO 2010/066789 | 6/2010 |
| WO | WO 2010/129324 | 11/2010 |
| WO | 2016/188538 A1 | 12/2016 |
| WO | 2016/188542 A1 | 12/2016 |
| WO | WO 2016/188537 | 12/2016 |
| WO | WO 2016/188539 | 12/2016 |
| WO | WO 2016/188540 | 12/2016 |
| WO | WO 2016/188541 | 12/2016 |

* cited by examiner

TIP PART FOR A VISION DEVICE

CROSS-REFERENCE TO RELATED APPLICATIONS

This application claims priority from European Patent Application No. 18190733, filed on Aug. 24, 2018, which application is incorporated herein by reference thereto.

FIELD OF THE DISCLOSURE

The present disclosure relates to vision devices such as, but not limited to, endotracheal tubes and endoscopes, more specifically to a tip part of such a vision device and a vision device such as an endoscope with such a tip part.

BACKGROUND

Vision devices such as endoscopes are well known for visually inspecting inaccessible places such as human body cavities. Typically, the endoscope comprises an elongated insertion tube with a handle at the proximal end, as seen from the operator, and visual inspection means, such as a built-in camera, at the distal end of the elongated insertion tube. This definition of the terms distal and proximal, i.e. proximal being the end closest to the operator and distal being the end remote from the operator, as used herein for endoscopes in general, is adhered to in the present specification. Electrical wiring for the camera and other electronics, such as LED lighting accommodated in the tip part at the distal end, run along the inside of the elongated insertion tube from the handle to the tip part. Instead of using cameras, endoscopes may also be fibre-optic, in which case the optical fibres run along the inside of the elongated insertion tube to the tip part. A working or suction channel may run along the inside of the insertion tube from the handle to the tip part, e.g. allowing liquid to be removed from the body cavity or allowing for insertion of surgical instruments or the like, into the body cavity. The suction channel may be connected to a suction connector, typically positioned at a handle at the proximal end of the insertion tube.

In order to be able to manoeuvre the endoscope inside the body cavity, the distal end of the endoscope may comprise a bending section with increased flexibility, e.g. a number of articulated segments of which the tip part forms the distal-most segment. The manoeuvring of the endoscope inside the body is typically done by tensioning or slacking pull wires also running along the inside of the elongated insertion tube from the tip part through the remainder of articulated segments to a control mechanism of the handle.

As the name indicates, endoscopes are used for seeing inside things, such as lungs or other human body cavities of a patient. Modern endoscopes are therefore typically equipped with a light source and a vision receptor including a vision sensor, such as a camera or an image sensor. Provided that sufficient light is present, it is possible for the operator to see where the endoscope is steered and to set the target of interest once the tip has been advanced thereto. This therefore normally requires illumination of the area in front of the distal tip of the endoscope, in particular the field of vision of the camera(s). The light source, such as a light emitting diode or an optical fibre, may provide illumination.

The illumination from the light source may result in an undesirable distribution of light, such as overexposure of the sides of the field of vision and underexposure of the centre of the field of vision, leading to poor vision quality.

A portion of light emitted from the light source may ingress into the vision sensor without being reflected by an outside object to be investigated. This type of light may be known as stray light. Stray light may cause unwanted optical artefacts in the image produced by the vision sensor and may generally reduce the quality of an image produced by the vision sensor.

Additionally, when, as in the present disclosure, the tip part is also intended for use in a disposable endoscope, reducing the manufacturing and assembly costs of the tip part are important.

Additionally, when, as in the present disclosure, the insertion tube of the endoscope is intended to be inserted into a human body cavity, the insertion tube furthermore needs to be sealed in a watertight manner. This is particularly the case for the distal tip part because it accommodates the camera, LED(s) and other delicate electronics, prone to malfunction or destruction if exposed to humidity.

On this background, it may be seen as an object of the present disclosure to provide a tip part with a new and improved optical arrangement.

One or more of these objects may be met by the present disclosure as described in the following.

SUMMARY OF THE DISCLOSURE

A tip part for an endoscope and an endoscope including the tip part are provided. A first aspect of the disclosure relates to a tip part for an endoscope. In some embodiments, the tip part comprises a vision receptor able to provide an image from light received from an object to be investigated; a first light source; an exterior housing accommodating the vision receptor and the first light source; a proximal or back end for connection to other parts of the vision device, such as an insertion tube of an endoscope; and a distal or front end for receiving light received from the object; the exterior housing comprising a window positioned at the distal end, the window being of a transparent material so that light received from the object can pass through the window to the vision receptor, and so that light emitted from the first light source can pass through the window to the exterior, the window comprising an exterior surface positioned at least partly in front of the vision receptor and the first light source, wherein the window integrally comprises a first optical well of the transparent material, the optical well being an interior protrusion positioned between the first light source and the vision receptor so that a portion of light emitted from the first light source and reflected from the exterior surface enters the first optical well, whereby stray light is at least partially prevented from entering the vision receptor.

This may provide the advantage that the manufacture of the tip part may be simplified by having a window which covers the light source and the vision receptor. Furthermore, the optical well, or trap, may improve the image quality of the vision receptor by trapping stray light being internally reflected in the window, which would otherwise propagate to the vision receptor. Furthermore, assembly of the tip part may be improved by providing the window with an integral optical well. The integral optical well may further increase the amount of stray light being trapped in the optical well.

The vision receptor may comprise a vision sensor, such as an image sensor. The vision receptor may comprise a lens or a plurality of lenses potentially arranged successively and optionally in a casing. The plurality of lenses may be arranged in front of the vision sensor, potentially so that an optical axis of the lens, potentially of the plurality of lenses, align or coincide with an optical axis of the vision sensor.

The plurality of lenses may be spaced by at least one spacer, potentially a plurality of spacers. The vision receptor may comprise a printed circuit board having at least one electrical component for converting light received by the vision receptor to an image. The exterior housing may accommodate the printed circuit board.

The exterior housing may further comprise an exterior side wall. The exterior side wall may extend from the distal end of the tip part to the proximal end of the tip part. The exterior side wall may extend from the window. The exterior side wall may extend along sides of the vision receptor and first light source. The exterior side wall may have a substantially cylindrical shape. The exterior side wall and window may be integrally formed. The exterior housing, potentially the exterior side wall of the exterior housing, may form a barrier or border between the exterior of the tip part and the interior of tip part. The exterior housing may define an internal volume, in which the vision receptor and the light source are positioned. The exterior housing may accommodate a working channel for supplying fluid to the distal end of the tip part, a printed circuit board of the vision receptor, and/or an image sensor of the vision receptor.

The tip part may comprise a working tube potentially forming part of the working channel of the endoscope. The exterior housing may accommodate the working tube. The working tube may be sealed in relation to the exterior housing, potentially so that fluid in the working tube may not ingress into the interior of the exterior housing.

The first optical well may be positioned so that a portion of stray light from the first light source, being internally reflected in the window, is redirected into the first optical well, whereby the portion of stray light may be internally reflected in the first optical well away from the vision receptor; absorbed in the first optical well, potentially by a light absorbing material surrounding the first optical well, such as a substantially opaque material and/or black material; and/or refracted out of the first optical well away from the vision receptor.

A material may be provided surrounding the first optical well. The material may be air; gas; glue; solid; light absorbing, such as partly or substantially completely opaque.

Additionally or alternatively, the first optical well may be an interior protrusion protruding in a direction from the window towards the vision receptor. The first optical well may be positioned on an interior surface of the window. The first optical well may be positioned between between the first light source and the vision receptor.

Additionally or alternatively, the first optical well may be a ridge between the first light source and the vision receptor. The ridge may extend transversely to an optical axis of the first light source and/or the vision receptor.

Additionally or alternatively, the light source or light source(s) may be an optical fibre or light emitting diode.

Additionally or alternatively, the tip part may comprise a second light source and a second optical well. The second light source and second optical well may be provided similarly as the first light source and optical well, respectively. The second light source and second optical well may be positioned on an opposite side of the vision receptor.

The window may have different shapes, such as circular, half-moon shaped etc. The window may comprise a plurality of window elements. The window elements may abut each other. The window elements may be fixed to each other, potentially by gluing or welding. The window may preferably be integrally formed in one piece.

Additionally or alternatively, the window may be a front window, potentially allowing the vision receptor to receive image information from the front of the tip part. The exterior surface of the window may be an exterior front surface.

Additionally or alternatively, the window may be a side window, for instance when the endoscope is a duodenum endoscope. The side window may allow the vision receptor to receive image information from a side, potentially from a radial direction, of the tip part. The exterior surface of the window may be an exterior side surface.

Additionally or alternatively, the window may comprise a front window and a side window.

The window may comprise, potentially consist essentially of, a transparent material. A transparent material will be able to transmit some image information and may potentially be defined as allowing at least 50% of light entering the window at the exterior surface to pass through the window. A transparent material will be able to transmit more image detail than a translucent material. The transparent material may be a polymer, glass, plastic polymer, or any other suitable material, e.g. silicone.

In this specification, stray light may be defined as light emitted from a light source, which ingresses into a vision receptor before being reflected by an outside or investigated object, for instance by internal reflections in the window. This may cause unwanted optical artefacts in the image produced by the vision receptor.

In this specification, a lens may be defined as a device having a lens effect. A lens effect may be defined as the ability of a lens to alter optical properties of light propagating through the lens, such as focusing, collimating, or dispersing the light.

In this specification, the term "in front of" when referring to the position of an element relative to an optical device, such as a lens, a vision receptor, and/or a light source, the element may be understood to be positioned so that the optical device has an optical effect on the element. For instance, a lens positioned in front of a light source may be understood so that the lens is positioned so that light emitted from the light source propagates directly through the lens.

In this specification, the term "to accommodate" may additionally or alternatively be defined as "to house" or "to enclose" or "to surround". For instance, the exterior housing may enclose or surround the vision receptor and/or the light source.

In this specification, the terms "integrally" or "integrally provided" or "integrally comprising" or similar may be defined as the associated features form an integral part of a whole; and/or be moulded in one piece; and/or be substantially inseparable by hand.

In this specification, the term "proximal" may be defined as being closest to the operator and the term "distal" as being remote from the operator. The term "proximal-distal axis" may be defined as an axis extending between these two extremes, in the present case the proximal-distal axis may be a centre axis of the tip part extending between a proximal extremity of the proximal end of the tip part and a distal extremity of the distal end of the tip part.

In this specification, the distal end of the tip part should not be construed to only comprise the most distal extremity of the tip part, rather the term "distal end of the tip part" should be understood as a portion of the tip part being distally positioned, e.g. a remaining portion of the tip part relative to the proximal or back end and/or a portion of the tip part for not being connected to other parts of the endoscope and/or a distally located half of the tip part. In some embodiments, the window may be a side window positioned at the distal or front end of the tip part.

In this specification, the term "interior" may be defined as being positioned in an interior space of the tip part, and the term "exterior" may be defined as being positioned in an exterior space of the tip part or as not being positioned in an interior space of the tip part.

In this specification, an endoscope may be defined as a device adapted for viewing bodily cavities and/or channels of a human and/or animal body. The endoscope may for instance be a conventional flexible or steerable endoscope or a rigid endoscope or an endotracheal tube potentially provided with a camera and light source for ensuring the correct position of the endotracheal tube, for instance a laryngoscope. The endoscope may be a duodenum endoscope.

Additionally or alternatively, the first optical well may be positioned at a distance in front of the first light source.

By providing the first optical well at a distance in front of the first light source, a greater portion of light emitted from the first light source may be captured in the first optical well.

The first light source may be positioned at a distance in a backward direction from the first optical well. The first light source may be positioned in front of a camera sensor of the vision receptor.

Additionally or alternatively, wherein the vision receptor may comprise a casing, potentially in the form of a lens barrel, positioned between the first light source and a vision sensor of the vision receptor, the casing includes a light shield configured to substantially prevent light from passing through the casing.

By providing a casing with a light shield between the first light source and the vision sensor, a portion of stray light may be absorbed thus increasing the image quality of the vision sensor.

The casing may encase the vision sensor and/or a lens or lenses of the vision receptor. The casing may extend along a proximal-distal axis of the tip part. The casing may be in the form of a lens barrel potentially substantially having the shape of a cylindrical shell. The light shield may be provided in the form of a light shielding layer provided on the casing. The light shielding layer may be provided by an adhesive, potentially hardened glue. The glue may be opaque, potentially black. The optical well may be positioned between the casing and the first light source.

Additionally or alternatively, the exterior front surface may be substantially planar, potentially having substantially no lens effect.

By having a planar window, lens effects of the window may be reduced, thus potentially ensuring uniform optical characteristics when different fluids, i.e. liquid(s) and/or gas(ses), are present in front of the window, for instance air or water.

Additionally or alternatively, the window is positioned at a distal end of the tip part.

Additionally or alternatively, the exterior housing may comprise an exterior side wall extending from the window along sides of the vision receptor and the first light source, the exterior side wall and window being integrally formed or being in one piece.

By integrally forming the exterior side wall and window, a sealed tip part may be provided. Additionally, the manufacture of the exterior housing may be made simpler as fewer parts are required.

The exterior side wall may enclose the interior of the tip part.

Additionally or alternatively, the exterior housing may essentially consist of the same material as the window.

Additionally or alternatively, the window comprises, potentially consists essentially of, a first material and the exterior housing comprises a second, different material, the window and exterior housing being integrally formed or being in one piece by a multiple, potentially two, component moulding process. This may provide the advantage that the first and second materials can be selected according to the desired properties, for instance a transparent material may be selected for the window and an opaque material may be selected for the exterior housing.

Additionally or alternatively, the vision receptor may comprise a lens, potentially a plurality of lenses, being arranged, potentially successively in the casing, between the vision sensor, potentially the image sensor, and the window.

Additionally or alternatively, the lens or plurality of lenses may be separate from the window. Additionally or alternatively, the lens or plurality of lenses is not an integral part of the window. Additionally or alternatively, the lens or plurality of lenses is made of a different material than the window.

Additionally or alternatively, the optical well may form a support collar or seat for the vision receptor so as to fix the position of the vision receptor in relation to the exterior housing.

This may provide the advantage that the mounting of the vision receptor in the exterior housing may be eased, as the optical well assists in centring the vision receptor.

Additionally or alternatively, the optical well may abut the vision receptor.

Additionally or alternatively, the first optical well may at least partially be surrounded by an opaque material, so that the first optical well is able to at least partially prevent stray light from entering the vision receptor by absorbing the stray light.

Additionally or alternatively, the first optical well may comprise a light exit, so that the first optical well is able to at least partially prevent stray light from entering the vision receptor by directing or refracting the stray light out of the light exit away from the window, potentially the vision receptor zone.

Additionally or alternatively, the window may comprise a first light source zone able to transmit light emitted from the first light source to outside of the tip part. The first light source zone may comprise a substantially planar first light reception end facing the first light source.

Additionally or alternatively, the first light source zone may be positioned between exterior front surface and the first light source. The first light source zone may have no lens effect.

Additionally or alternatively, the window may comprise a vision receptor zone able to transmit light received from outside the window to the vision receptor, the vision receptor zone potentially comprises a substantially planar abutment surface facing the front of the vision receptor.

Additionally or alternatively, the vision receptor zone potentially may be positioned between the exterior front surface and the vision receptor. The vision receptor zone may have no lens effect.

Additionally or alternatively, the first optical well is positioned between the first light source zone and the vision receptor zone.

Additionally or alternatively, the window may comprise a first light guide positioned in front of the first light source, potentially directly in front of the first light source.

Additionally or alternatively, The first light guide may be of a transparent material, potentially the same material as the window. The first light guide may have a predetermined length between at least one first light reception end adapted for receiving light from the first light source and at least one second light emission end adapted to emit light. The first light guide may form an integral part of the exterior housing. By integrating the light guide in the exterior housing, it becomes possible to provide a sealed front end of the tip part and at the same time provide a well-defined exit viewing angle for the light from the light source.

Additionally or alternatively, The predetermined length may comprise an expanding sector and/or a narrowing sector in which the light guide has a varying cross-sectional area along the predetermined length, wherein, in said expanding sector, the cross-sectional area is monotonously increasing in the direction from the at least one light reception end towards the at least one light emission end and in said narrowing sector, the cross-sectional area is monotonously decreasing. By providing a monotonously changing cross-sectional area over at least a section of the predetermined length, it becomes possible to provide a desired light distribution profile, matching e.g. the field of vision of the vision receptor.

Additionally or alternatively, the cross-sectional area may have, along at least a part of the predetermined length, the shape of a rectangle. A substantially rectangular shape is preferable, potentially with rounded corners, because the vision receptor will normally comprise a rectangular field of vision. By also having a rectangular cross sectional shape of the light guide, the desired light distribution profile may be made to match at least partially the field of vision of the vision receptor. Thus, more light is available in the corners. Potentially, also less light is wasted.

Additionally or alternatively, the first optical well and/or second optical well may have a width measured in a substantially outwardly direction, potentially a radial direction, less than 1 mm, 0.9 mm, 0.8 mm, 0.7 mm, 0.6 mm, 0.5 mm, 0.4 mm, 0.3 mm, or 0.25 mm.

The outwardly direction may be a radial direction of the tip part, potentially orthogonal to the proximal-distal axis. When the optical well is a ridge the width may be the width of the ridge.

Additionally or alternatively, the first optical well and/or second optical well may have a depth and a width, the depth may be at least 1 times, 1.5 times, 2 times, or 3 times greater than the width, the width may be measured in a substantially outwardly direction, potentially a radial direction of the tip part, the depth may be measured in the proximal-distal direction, potentially an axial direction of the tip part.

Additionally or alternatively, the first light guide and/or second light guide may have a width measured in a substantially outwardly direction, potentially a radial direction, less than 5 mm, 4 mm, 3 mm, 2 mm, or 1 mm.

Additionally or alternatively, a width of the first light guide and/or second light guide divided by the width of the first optical well and/or second optical well may be at least 1.5, 2.0, 2.5, 3.0, or 3.5.

Additionally or alternatively, a length of the first optical well and/or second optical well in a proximal-distal axis may be 50%, 40%, 30%, 20%, or 10% of the length of the first light guide and/or second light guide.

Additionally or alternatively, a distance normal to the optical axis of the light source between the associated light guide and the associated optical well is 10%, 20%, 30%, 40%, 50%, 60%, 70%, 75%, 80%, 90%, or 100% of the width of the associated optical well.

Additionally or alternatively, a distance between the optical axis of the light source and the associated optical well may be 1 times, 2 times, 3 times, 4 times, or 5 times the width of the associated optical well, the distance may be normal to the optical axis of the light source.

Additionally or alternatively, an endoscope may comprise a tip part according to the first aspect of the disclosure. The endoscope may comprise an elongated insertion tube with a handle at the proximal end. The tip part may be positioned at the distal end of the elongated insertion tube. The tip part may further comprise a bending section positioned between the tip part and the elongated insertion tube. The bending section may be configured to articulated, so as to manoeuvre the endoscope inside a body cavity.

A person skilled in the art will appreciate that any one or more of the above aspects of the disclosure and embodiments thereof may be combined with any one or more of the other aspects of the disclosure and embodiments thereof.

BRIEF DESCRIPTION OF DRAWINGS

The disclosure will now be described in greater detail based on non-limiting exemplary embodiments and with reference to the drawings, on which.

DETAILED DESCRIPTION

Figure 1A:
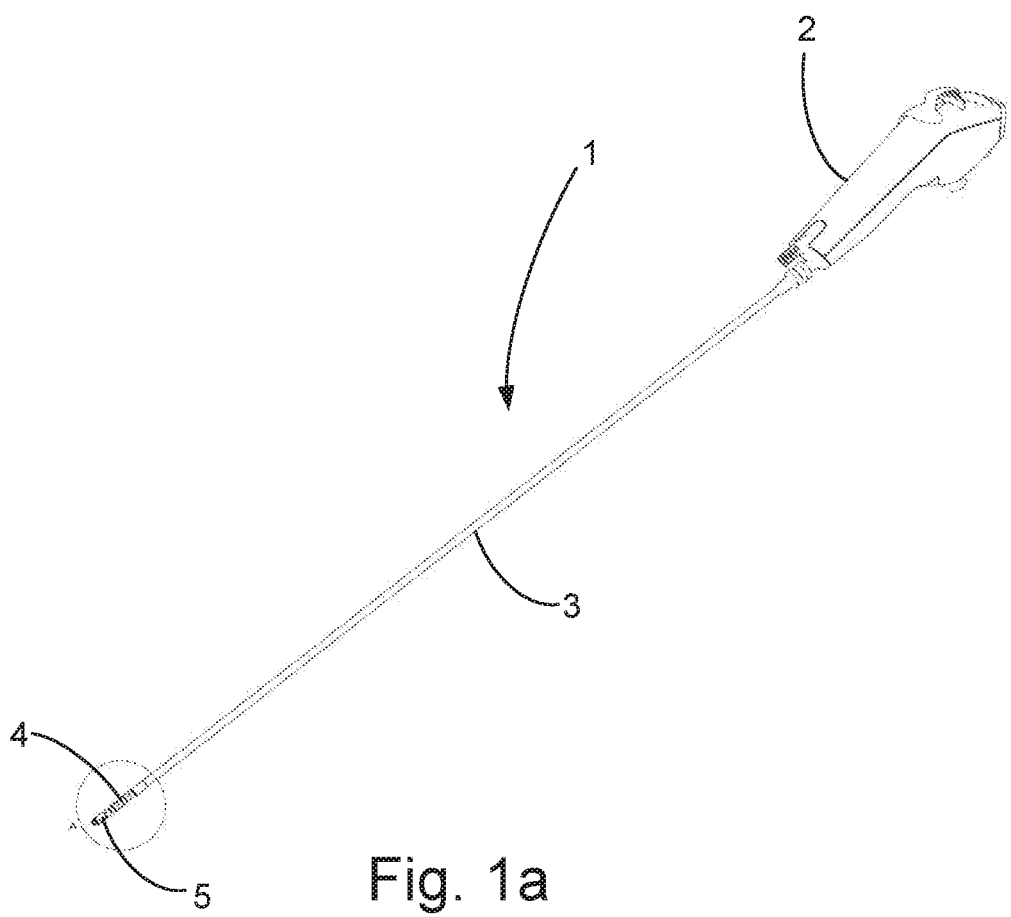
FIG. 1a shows a perspective view of an endoscope in which a tip part according to the present disclosure is implemented.

Turning first to FIG. 1a, an endoscope 1 exemplifying the vision device according to the disclosure is shown. The endoscope 1 comprises a handle 2 at the proximal end of the endoscope 1, an insertion tube 3 extending towards the distal end of the endoscope 1 where it comprises an articulated bending section 4, which, as the most distal segment, has a distal tip part 5 according to the disclosure. Though omitted for illustration purposes, the articulated bending section 4 will normally be covered by a suitable sleeve connected at least at its own distal end to the distal tip part 5, e.g. by means of an adhesive. The tip part 5 of the present disclosure is intended as a tip part 5 for a disposable endoscope 1 to be thrown away after use and therefore low manufacturing costs are an important issue.

Figure 1B:
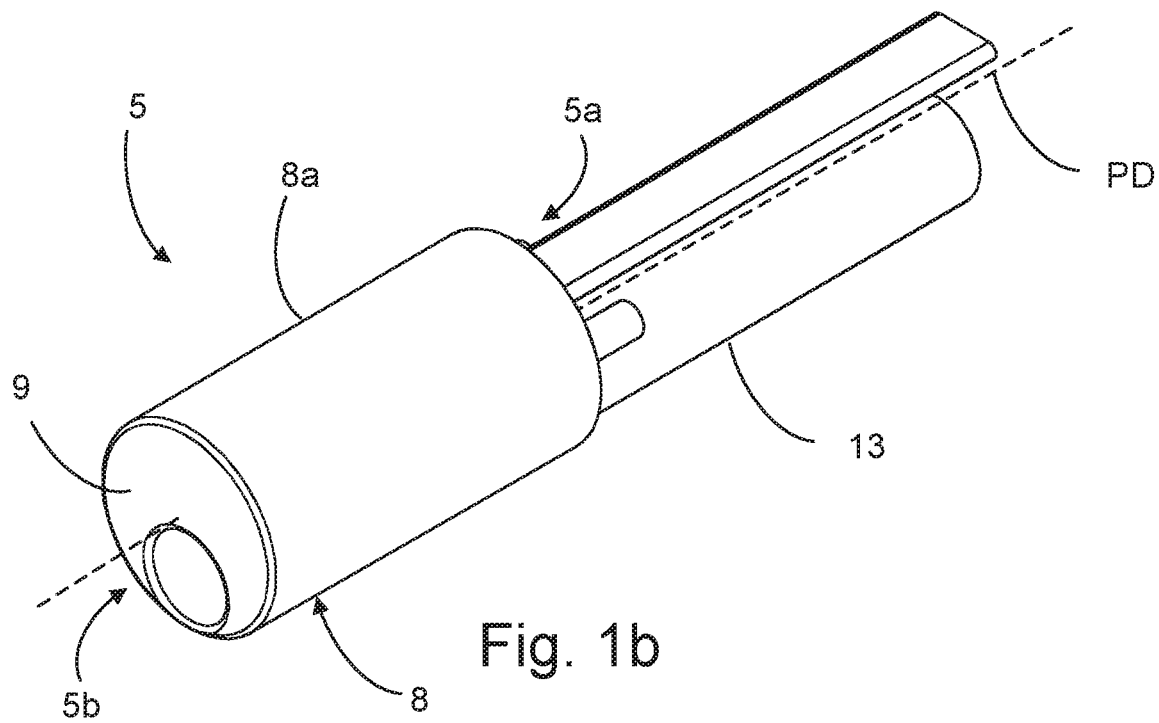
FIG. 1b shows a perspective view of a tip part according to the first aspect of the present disclosure.

FIG. 1b shows a detailed embodiment of a tip part 5 for the endoscope shown in FIG. 1a. The tip part 5 has a proximal end 5a for connection to the insertion tube 3 of endoscope 1 and a distal end 5b for receiving light from the object (not shown). The tip part 5 further comprises an exterior housing 8 including a window 9, which is positioned at the distal end 5b of the tip part 5, and an exterior side wall 8a extending along a proximal-distal axis PD. The exterior side wall 8a and window 9 are integrally formed in one piece. The exterior housing forms a barrier between the exterior of the tip part 5 and the interior of tip part 5. Also connected and sealed to the exterior housing is a tube 13 forming part of the working channel of the endoscope 1. In the illustrated embodiment, the tube 13 is connected via a pair of protrusions between which the tube 13 is held with the aid of an adhesive as seen in FIG. 2b.

Figure 2A:
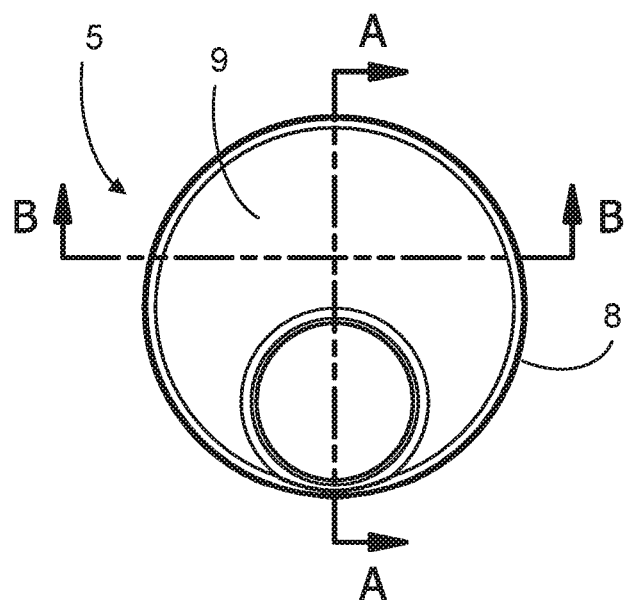
FIG. 2a shows a front view of a distal end of the tip part of FIG. 1b.

FIG. 2a shows the position of a first cross-sectional line A-A and the position of a second cross-sectional line B-B on the tip part 5 of FIG. 1b. Cross section A-A is shown in FIG. 2b and cross section B-B is shown in FIG. 3.

Figure 2B:
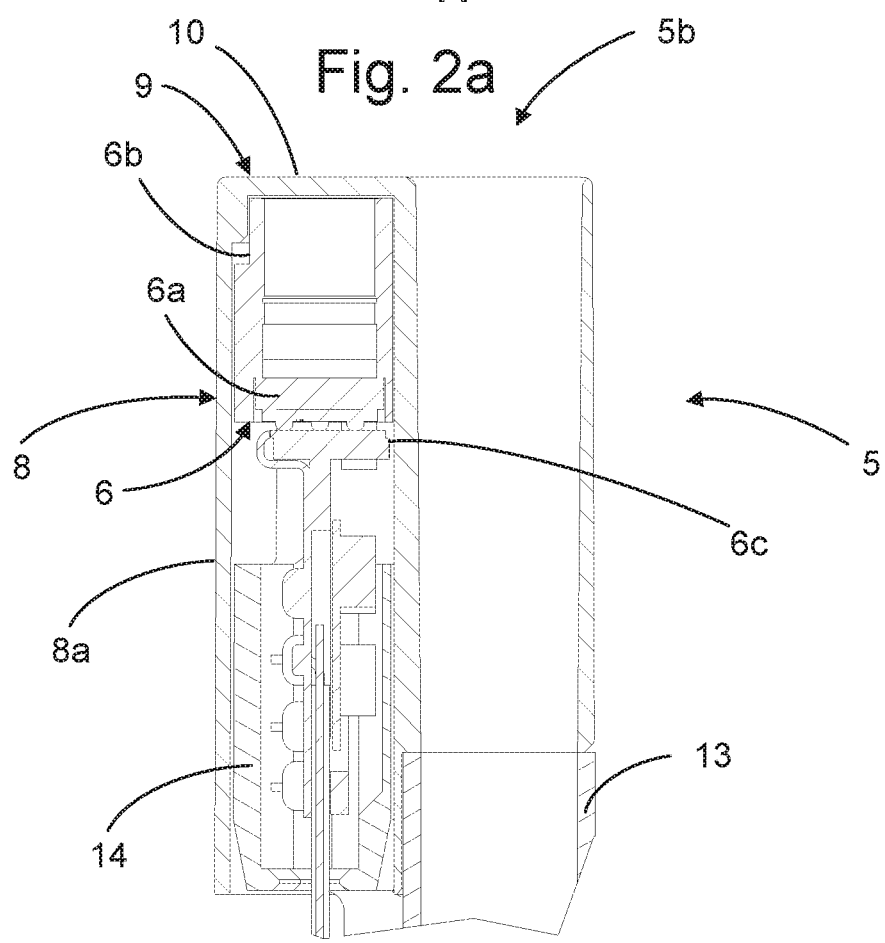
FIG. 2b shows a half cross-sectional view of the tip part along the line A-A of FIG. 2a, FIG. 3 shows a half cross-sectional view of the tip part along the line B-B of FIG. 2a, FIG. 4 shows a perspective view of a topmost quarter cross-section of the tip part along the lines A-A and B-B of FIG. 2a and hatching on the cross-sectional faces is here omitted.

As seen in FIG. 2b, the tip part 5 comprises a vision receptor 6 configured to provide an image from light received from an object to be investigated, such as a human body cavity. The vision receptor 6 comprises an image or vision sensor 6a, a plurality of lenses (not shown), and a printed circuit board 14 with electrical components, so that the vision receptor can convert the received light to a digital image. The casing 6b is in the form of a lens barrel provided with a light shielding layer in the form of an opaque outer surface so as to prevent light from ingressing into the vision receptor 6.

Figure 3:
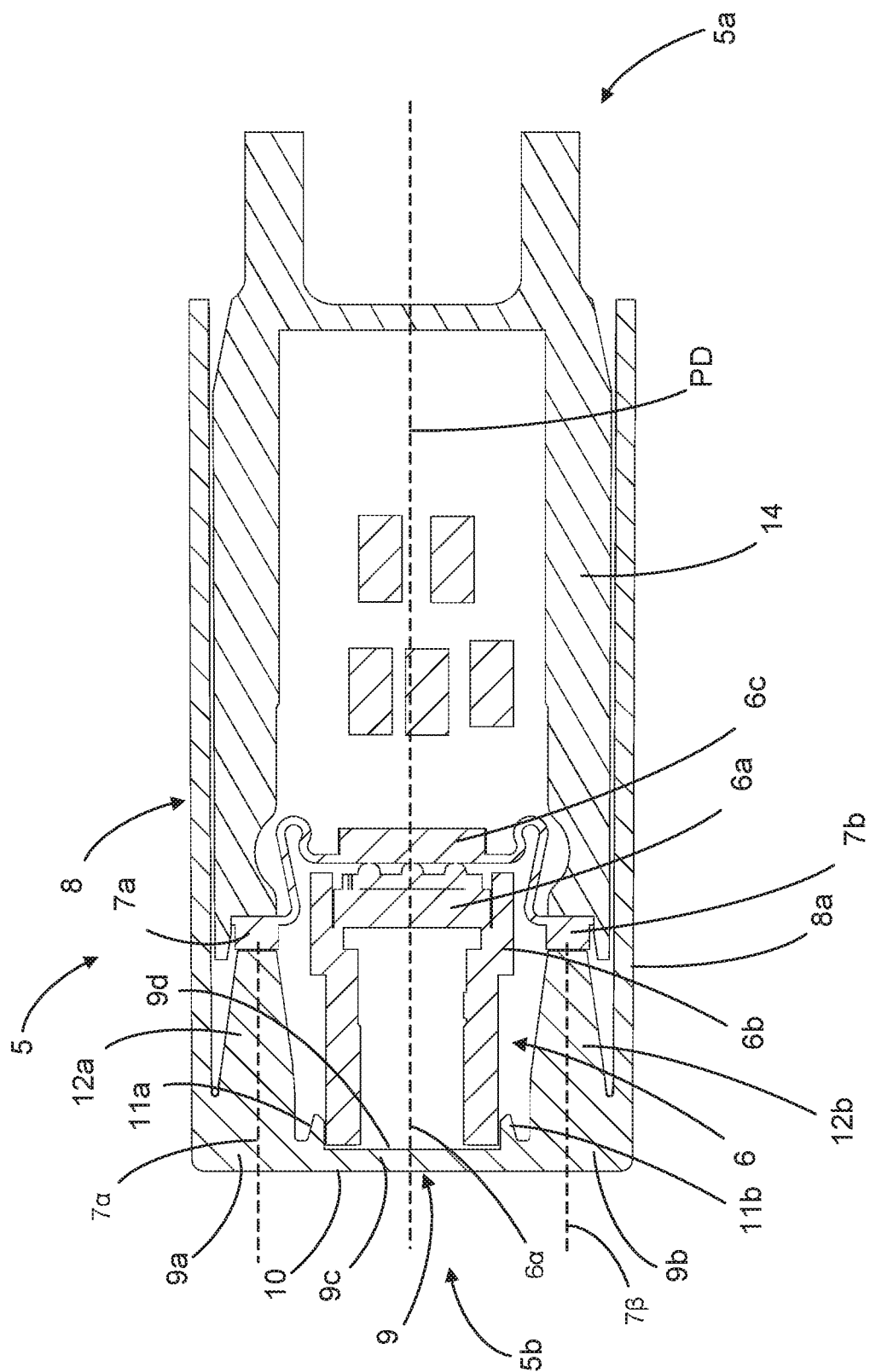

Turning to FIG. 3, the tip part 5 comprises two light sources 7a, 7b in form of LEDs positioned on opposite sides of the vision receptor 6. The vision sensor 6a, plurality of lenses (not shown), casing 6b, printed circuit board 6c, and the two light sources 7a, 7b are accommodated in the exterior housing 8. The exterior side wall 8a of the exterior housing 8 extends from the window 9 along sides of the vision sensor 6a, the plurality of lenses (not shown), the casing 6b, the printed circuit board 6c, and the two light sources 7a, 7b. The light sources 7a, 7b are configured to emit light along optical axes 7α, 7β parallel to the proximal-distal axis PD.

The window 9 is made of a transparent rigid polymer material. The window 9 comprises a planar exterior front surface positioned directly in front of the vision receptor 6 and the light sources 7a, 7b, so that light received from the object can pass through the window 9 to the vision sensor 6a of the vision receptor 6, and so that light emitted from the light sources 7a, 7b can pass along an optical axis through the window 9 to the outside of the tip part 5.

The window 9 comprises a first and a second light source zone 9a, 9b configured to transmit light emitted from the first and second light source 7a, 7b to outside of the tip part 5. The light source zone 9a, 9b are positioned between the exterior front surface 10 of the window 9 and the vision receptor 6.

The window 9 further integrally comprises a first and second light guide 12a, 12b respectively, positioned directly in front of the first and second light source 7a, 7b, and adjacent to the light source zones 9a, 9b. The light guides 12a, 12b are in direct optical connection with the respective light source zones 9a, 9b. The light guides 12a, 12b are preferably made of the same transparent material as the window 9. The light guides 12a, 12b each have a predetermined length between a light reception end 12a', 12b' adapted for receiving light from the light source 7a, 7b and an end at the light source zone 9a, 9b adapted to emit light. The predetermined length comprises an expanding sector in which the light guides 12a, 12b has a varying cross-sectional area along the predetermined length. In said expanding sector, the cross-sectional area is monotonously increasing in the direction from the light reception end 12a', 12b' towards the light source zone 9a, 9b. The cross-sectional areas have, along at least a part of the predetermined length, substantially the shape of a rectangle with rounded corners.

The window 9 comprises a vision receptor zone 9c able to transmit light received from outside the window 9 to the vision receptor 6, the vision receptor zone comprises a substantially planar abutment surface 9d facing the vision receptor 6. The abutment surface 9d is an interior surface of the window 9 onto which the casing 6b abuts and rests. The vision receptor zone 9c has no lens effect.

The window 9 integrally comprise two optical wells 11a, 11b of the same transparent material as the window 9. The optical wells 11a, 11b are formed as an interior ridge with a proximal end, that is directed towards the proximal end of the tip part 5. The optical wells 11a, 11b are positioned between the light sources 7a, 7b and the vision receptor 6, respectively. The optical wells 11a, 11b are positioned at a distance in front of the light sources 7a, 7b and adjacent to the casing 6b of the vision receptor 6. The optical wells 11a, 11b are positioned between the respective light source zones 9a, 9b and the vision receptor zone 9c.

A portion of the light emitted from the light sources 7a, 7b is internally reflected in the window 9 and enters the optical wells 11a, 11b. The portion of light is then internally reflected and refracted in the optical wells 11a, 11b away from the vision receptor zone 9c through light exits positioned at the proximal end of the optical wells 11a, 11b. Additionally, the portion of light is absorbed by an opaque coating on the optical wells 11a, 11b. The opaque coating is provided by applying a glue which hardens into a substantially completely opaque coating. In the present embodiment, the light exits are provided with a coating having low internal reflectiveness. This allows stray light to be at least partially prevented from entering the vision receptor and the image quality to be improved.

In the present embodiment, the exterior side wall, the window, the light guide, the first optical well are molded in a single-piece. The purpose of the light exit of the first light well is to let light exit the well (refract) in this area where it is uncritical for the image. The first optical well extends proximally in a longitudinal direction from an internal surface of the window by at least 0.2 mm. The exterior side wall has a substantially circular cross-section with an external diameter less than 0.7 mm, and wherein the light guide is radially spaced apart from the first optical well by less than 0.2 mm. Preferably the external diameter is less than 0.7 mm and the light guide is radially spaced apart from the first optical well by less than 0.17 mm. Optimum length and width of the lightguide is dictated by the light emitting area of the LED. In the present embodiment, a width of the lightguide is about 0.5-0.7 mm in the narrow end, about 0.8-1.0 mm in the wide end, and has a length of about 0.8-1.5 mm. A longer light guide may be made by adding a cylindrical portion to maintain the collimating effects resulting from these dimensions.

To obtain a low cost suitable to produce single-use medical devices, it is desirable to minimize manufacturing labor by combining parts during molding processes. The combination of parts must balance the desire for clarity (window, light guide), with molding pressures and resulting part tension. In a variation of the present embodiment, the exterior side wall, the light guide, and the first optical well are molded in a single-piece. This decouples the competing manufacturing variables and enables use of an independently made window. The window is affixed to the single-piece comprising the exterior side wall, the light guide, and the first optical well. In another variation of the present embodiment, the window, the light guide, and the first optical well are molded in a single-piece. This enables molding of a transparent material without significant depth, relative to the side wall of the exterior housing, which facilitates molding of the single piece. The exterior side wall is affixed to the single-piece comprising the window, the light guide, and the first optical well. In yet another variation of the present embodiment, the window and the light guide are molded in a first single-piece, and the exterior side wall and the first optical well are molded in a second single-piece affixed to the first single-piece.

The tip part further comprises an interior housing 14 positioned inside the exterior housing 8. The interior housing 14 does not provide sealing for the internal parts of the tip part 5, e.g. the printed circuit board. Sealing of the printed circuit board may be provided by embedding the printed circuit board in hardened adhesive. The interior housing 14 provides a simple way of assembling some electronic parts of the tip part 5 prior to final assembly of the tip part.

Figure 4:
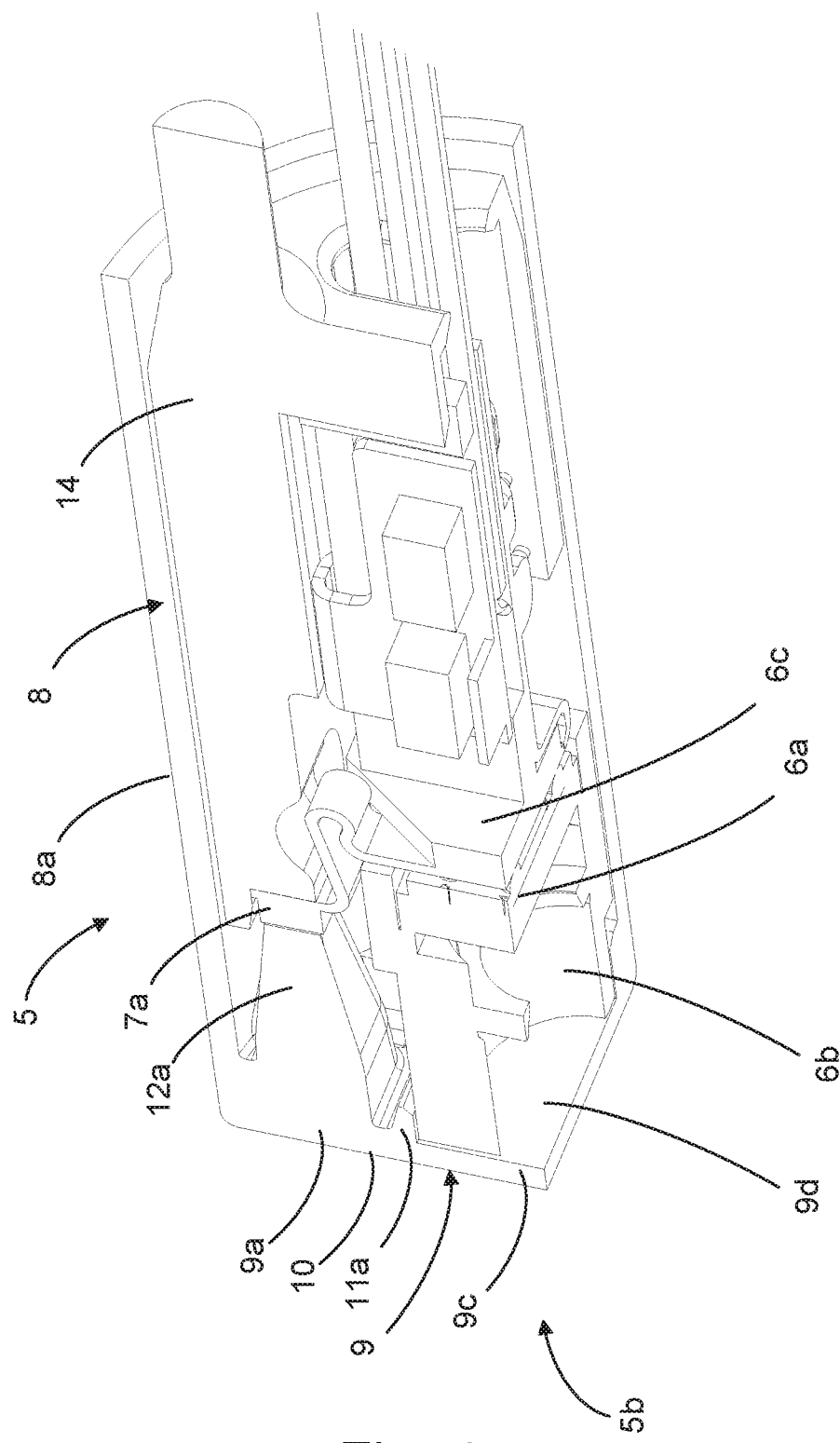

Turning to FIG. 4, the plurality of lenses (not shown) are to be arranged successively in the casing 6b between the abutment surface 9d and the vision sensor 6a.

Figure 5:
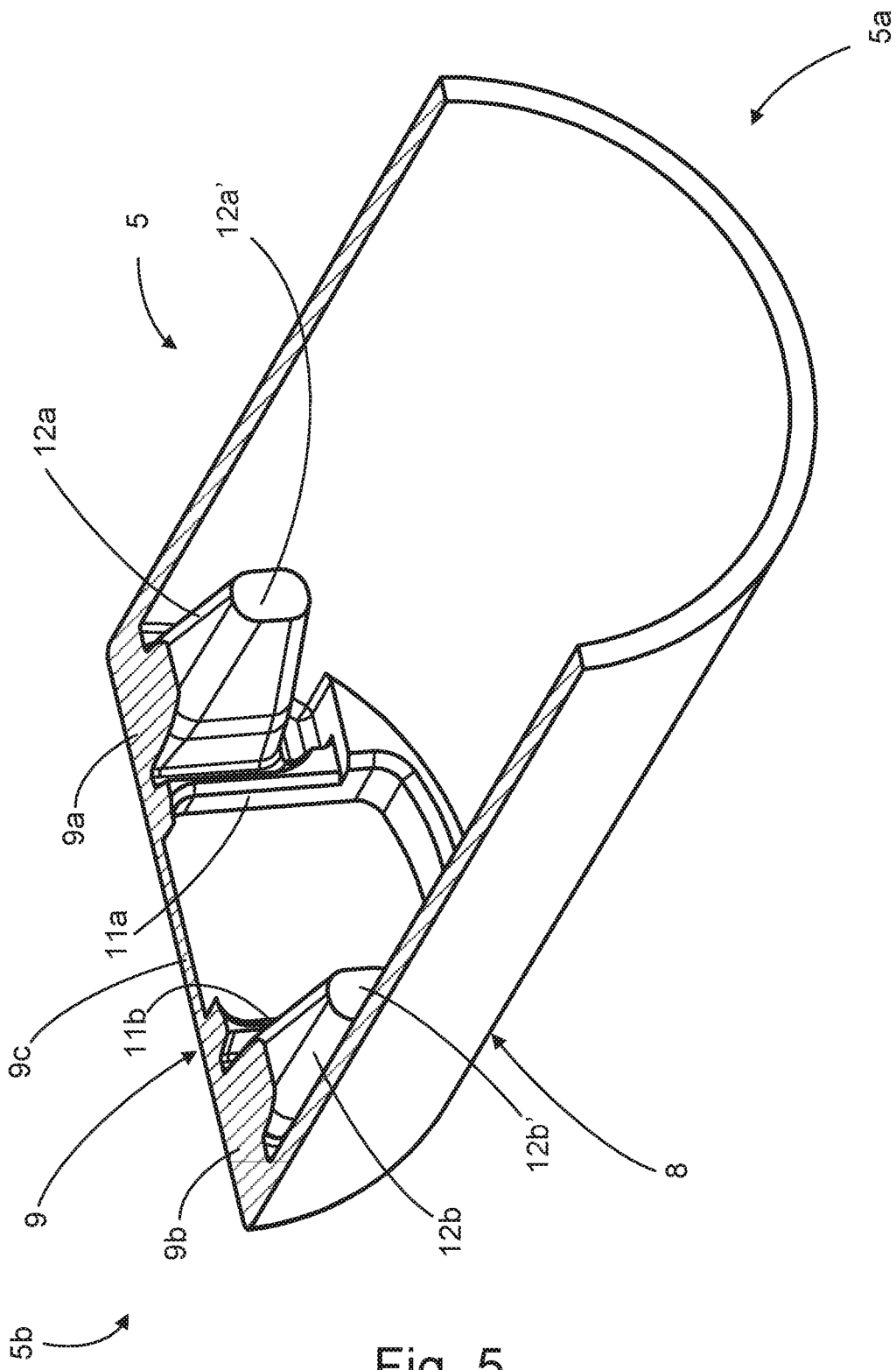
FIG. 5 shows a perspective view of a half cross-section of an exterior housing and window along the lines A-A of FIG. 2a without internal other internal parts of the tip part.

As best seen in FIG. 5, the optical wells 11a, 11b form a support collar or seat for the vision receptor so as to fix the position of the vision receptor in relation to the exterior housing.

To assemble the tip part, a front end of the tip part comprising the window, light guide, and light well is assembled in accord with various embodiments, where these components are molded together in in various combinations. An electronics assembly is then assembled including the circuit board and the vision receptor. The electronics assembly is then inserted through the proximal end of the exterior side wall of the housing until the casing is a desired distance from the window. The casing may abut the window to minimize stray light entry therefrom. The electronics assembly may be press-fit or bonded in or to the side wall.

LIST OF REFERENCES

The following is a list of reference numerals used throughout this specification.
1 endoscope
2 handle
3 insertion tube
4 bending section
5 tip part
5a proximal end
5b distal end
6 vision receptor
6a vision sensor
6b casing
6c printed circuit board
6a optical axis of vision receptor
7a first light source
7a optical axis of first light source
7b second light source
8 exterior housing
8a exterior side wall
9 window
9a first light source zone
9b second light source zone
9c vision receptor zone
9d abutment surface
10 exterior front surface
11a first optical well
11b second optical well
12a first light guide
12a' first light reception end
12b second light guide
12b' second light reception end
13 tube
14 interior housing
PD proximal-distal axis

I claim:

1. A tip part for an endoscope, the tip part comprising:
a proximal end longitudinally opposite and spaced apart from a distal end;
a vision receptor including a vision sensor and a casing, the vision sensor able to provide an image from light received from an object to be investigated, and the casing positioned distally of and longitudinally aligned with the vision sensor;
a first light source;
a first light guide;
an exterior housing accommodating the vision receptor, the first light guide, and the first light source;
a window positioned at the distal end of the tip part, the window being of a transparent material so that light received from the object can pass through the window to the vision receptor, and so that light emitted from the first light source can pass through the light guide and the window to an exterior, the window comprising an exterior front surface positioned at least partly in front of the vision receptor and the first light source; and
a first optical well positioned transversely between the first light guide and the casing and extending proximally from the window so that a portion of light emitted by the first light source and reflected from the window enters the first optical well and is thereby at least partially prevented from entering the vision receptor,
wherein the first light guide is positioned longitudinally between the first light source and the window.

2. The tip part of claim 1, wherein the first optical well is positioned at a distance in front of and longitudinally spaced apart from the first light source.

3. The tip part of claim 1, wherein the casing includes a light shield configured to substantially prevent light from passing through the casing.

4. The tip part of claim 1, wherein the exterior housing comprises an exterior side wall extending from the window along sides of the vision receptor and the first light source, the exterior side wall and window being integrally formed or being in one piece.

5. The tip part of claim 1, wherein the optical well forms a support collar for the vision receptor so as to fix a position of the vision receptor in relation to the exterior housing.

6. The tip part of claim 1, wherein the first optical well is at least partially surrounded by an opaque material, so that the first optical well is able to at least partially prevent stray light from entering the vision receptor.

7. The tip part of claim 1, wherein the first optical well comprises a light exit configured to direct light away from the window.

8. The tip part of claim 1, wherein the window comprises a first light source zone able to transmit light emitted from the first light source to outside of the tip part, the first light source zone comprises a substantially planar first light reception end facing the first light source.

9. The tip part of claim 1, wherein the first optical well has a width, measured in a substantially outwardly radial direction, less than 0.4 mm.

10. The tip part of claim 9, wherein the first light guide has a proximal end, a distal end spaced apart from the proximal end, and a width measured at the distal end in a substantially outwardly radial direction, less than 2 mm.

11. The tip part of claim 10, wherein the width of the first light guide divided by the width of the first optical well is at most 3.5.

12. The tip part of claim 1, wherein the exterior side wall, the first light guide, and the first optical well are molded in a single-piece, and wherein the window is affixed to the single-piece comprising the exterior side wall, the first light guide, and the first optical well.

13. The tip part of claim 1, wherein the exterior side wall is affixed to the single-piece comprising the window, the light guide, and the first optical well.

14. The tip part of claim 1, wherein the window and the light guide are molded in a first single-piece, and wherein the exterior side wall and the first optical well are molded in a second single-piece affixed to the first single-piece.

15. An endoscope, comprising: a tip part according to claim 1.

16. The tip part of claim 12, wherein the first optical well extends proximally in a longitudinal direction from an internal surface of the window by at least 0.2 mm.

17. The tip part of claim 16, wherein the exterior housing comprises an exterior side wall extending proximally from the window along sides of the vision receptor and the first light source, wherein the exterior side wall has a substantially circular cross-section with an external diameter less than 0.7 mm, and wherein the first light guide is radially spaced apart from the first optical well by less than 0.2 mm.

18. An endoscope comprising:
a tip part according to claim 1;
an insertion portion connected to the tip part; and
a handle connected to the insertion portion,
wherein the first optical well comprises a protrusion extending from the window and having a length along a longitudinal direction greater than 0.2 mm, the first optical well spaced apart from the first light guide by a gap greater than 0.1 mm.

19. The endoscope of claim 18, wherein the exterior side wall has a substantially circular cross-section with an external diameter less than 0.7 mm.

20. The endoscope of claim 19, wherein the exterior side wall, the light guide, and the first optical well are molded in a single-piece, and wherein the window is affixed to the single-piece comprising the exterior side wall, the light guide, and the first optical well.

21. The endoscope of claim 19, wherein the window, the light guide, and the first optical well are molded in a single-piece, and wherein the exterior side wall is affixed to the single-piece comprising the window, the light guide, and the first optical well.

22. The endoscope of claim 19, wherein the window and the light guide are molded in a first single-piece, and wherein the exterior side wall and the first optical well are molded in a second single-piece affixed to the first single-piece.

* * * * *